US005783387A

United States Patent [19]

Lucas et al.

[11] Patent Number: 5,783,387
[45] Date of Patent: Jul. 21, 1998

[54] METHOD FOR IDENTIFYING AND QUANTIFYING NUCLEIC ACID SEQUENCE ABERRATIONS

[75] Inventors: Joe N. Lucas, San Ramon; Tore Straume, Tracy; Kenneth T. Bogen, Walnut Creek, all of Calif.

[73] Assignee: The Regents of the University of California, Oakland, Calif.

[21] Appl. No.: 384,497

[22] Filed: Feb. 6, 1995

[51] Int. Cl.⁶ .............. C12Q 1/68; C07H 21/02; C07H 21/04; C12N 15/00
[52] U.S. Cl. ............ 435/6; 536/23.1; 536/24.3; 935/77; 935/78
[58] Field of Search ............... 435/6; 536/23.1, 536/24.3; 935/77, 78

[56] References Cited

U.S. PATENT DOCUMENTS

| | | |
|---|---|---|
| 4,358,535 | 11/1982 | Falkow et al. |
| 4,376,110 | 3/1983 | David et al. |
| 4,478,914 | 10/1984 | Giese |
| 4,486,539 | 12/1984 | Ranki et al. |
| 4,894,325 | 1/1990 | Englehardt et al. |
| 5,209,919 | 5/1993 | Turteltaub et al. ............ 424/1.1 |
| 5,273,882 | 12/1993 | Snitman et al. |
| 5,374,524 | 12/1994 | Miller ............................ 435/6 |
| 5,424,413 | 6/1995 | Hogan et al. ............... 536/24.31 |
| 5,451,503 | 9/1995 | Hogan et al. ............... 536/24.31 |

FOREIGN PATENT DOCUMENTS

| | | |
|---|---|---|
| 0 063 879 | 11/1982 | European Pat. Off. |
| 0 097 373 | 1/1984 | European Pat. Off. |
| 0 151 492 | 8/1985 | European Pat. Off. |
| WO 85/04674 | 10/1985 | WIPO |

OTHER PUBLICATIONS

Funkakoshi, et al., *J. of Chromatography* 638:21–27 (1993).
Gildea, et al., *Tetrahedron Letters* 31:7095–7098 (1990).
Hobart, et al., *J. Immunological Methods* 153:93–98 (1992).
Jayabaskaran, et al., *Preparative Biochemistry* 17(2):121–141 (1987).
Lin, et al., *J. Org. Chem.* 56:6850–6856 (1991).
Ph.D. Thesis of W.–C. Lin, U.C. Riverside, (1990).
Lucas, et al., *International Journal of Radiation Biology* 56:35–44 (1989), 62:53–63 (1992).
Tkachuk, et al., *Science* 250:559–562 (1990).
GIBCO BRL TRIzol™ Reagent (Life Technologies, Gaithersburg, M.D.).
The Stratagene Catalog p. 39 (1988).
Dunn et al. Cell 12(1) : pp. 23–36 (1977).
"Basic Methods in Molecular Biology," Ed. Davis et al. Elsevier Sci. Pub. pp. 75–78 (1986).
The Oncor Catalog (1992–1993).
Leary et al., PNAS 80:4045–4049 (1983).
Pinkel et al., PNAS 83:2934–2938 (1986).
Pinkel et al., PNAS 85:9138–9142 (1988).
Mouton et al., Archives of Biooch. and Biophy. 218:101–108 (1982).
Vooijs et al. Am. J. Hum. Genet. 52:586–597 (1993).
Landegren et al. Science 241:1077–1080 (1988).
Langdale et al. Gene 36:201–210 (1985).
Matthews et al. Analytical Biochem. 169:1–25 (1988).

*Primary Examiner*—Kenneth R. Horlick
*Assistant Examiner*—Ethan Whisenant
*Attorney, Agent, or Firm*—Henry P. Sartorio

[57] ABSTRACT

A method for detecting nucleic acid sequence aberrations by detecting nucleic acid sequences having both a first and a second nucleic acid sequence type, the presence of the first and second sequence type on the same nucleic acid sequence indicating the presence of a nucleic acid sequence aberration. The method uses a first hybridization probe which includes a nucleic acid sequence that is complementary to a first sequence type and a first complexing agent capable of attaching to a second complexing agent and a second hybridization probe which includes a nucleic acid sequence that selectively hybridizes to the second nucleic acid sequence type over the first sequence type and includes a detectable marker for detecting the second hybridization probe.

51 Claims, 5 Drawing Sheets

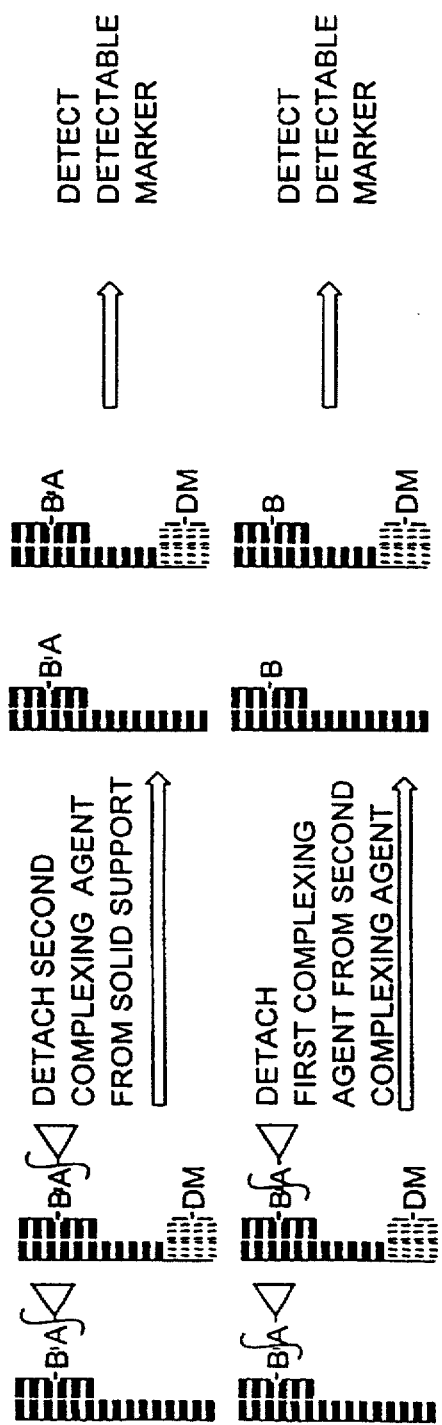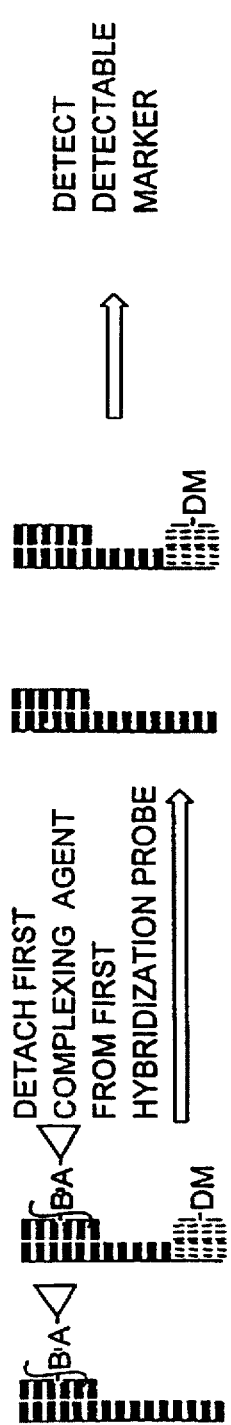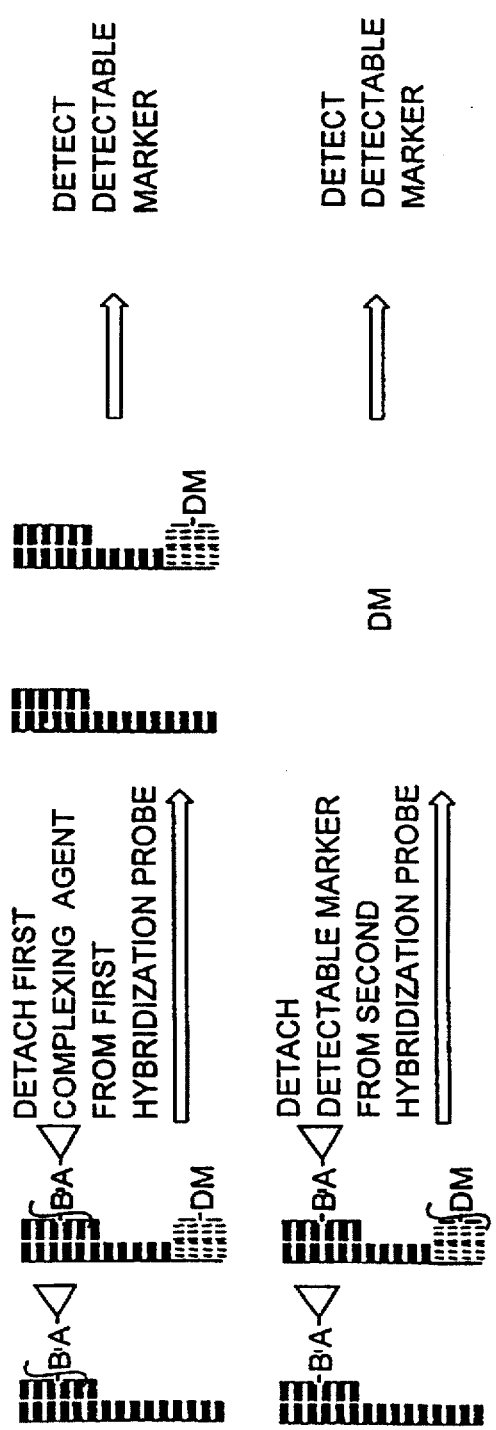
FIG. 3D
FIG. 3E
FIG. 3F
FIG. 3G

METHOD FOR IDENTIFYING AND QUANTIFYING NUCLEIC ACID SEQUENCE ABERRATIONS

The United States government has rights in this invention pursuant to Contract Number W-7405-ENG-48 between the United States Department of Energy and the University of California for the operation of Lawrence Livermore National Laboratory.

BACKGROUND OF THE INVENTION

1. Field of the Invention

The present invention relates to a method for identifying nucleic acid sequences using hybridization probes. More specifically, the present invention relates to a method for identifying and quantifying nucleic acid sequence aberrations using hybridization probes.

2. Description of Related Art

Hybridization probes are widely used to detect and/or quantify the presence of a particular nucleic acid sequence within a sample of nucleic acid sequences. Hybridization probes detect the presence of a particular nucleic acid sequence, referred to herein as a target sequence, through the use of a complimentary nucleic acid sequence which selectively hybridizes to the target nucleic acid sequence.

In order for a hybridization probe to hybridize to a target sequence, the hybridization probe must contain a nucleic acid sequence that is at least partially complementary to the target sequence. The complementary sequence must also be sufficiently long so that the probe exhibits selectivity for the target sequence over non-target sequences.

In order to design a hybridization probe that selectively hybridizes to a target sequence, one must first determine a nucleic acid sequence that is at least partially complementary to the target sequence. In applications where the target sequence is already known, for example, where one seeks to detect the insertion of a gene or promoter sequence into a vector or plasmid, a variety of methods are known for preparing highly selective hybridization probes. However, one limitation of hybridization assays is that one does not also know the target sequence in sufficient detail to prepare a selective hybridization probe.

Hybridization assays are most commonly designed to detect the presence or absence of a particular nucleic acid sequence, for example the insertion of a gene into a vector or plasmid. However, hybridization assays are generally not designed to detect the movement of a nucleic acid sequence relative to another nucleic acid sequences in a sample. The detection of nucleic acid sequence aberrations using a hybridization assay is limited by both the ability to design sequence specific probes and the ability to detect the movement of a nucleic acid sequence relative to other nucleic acid sequences in a sample. The detection of nucleic acid sequence aberrations is further limited by the infrequency of nucleic acid sequence aberrations. For example, chromosome translocations, a type of nucleic acid sequence aberration, is estimated to occur at a frequency on the order of 1 per 1,000,000 cells in a particular gene. Currently available hybridization assays are not able to accurately detect and quantify such infrequent genetic events. Although translocations are more frequent in the whole genome (approximately 1 per 200 cells), currently available assays are not able to quantify the large number of individuals that must be evaluated in population studies.

As used herein, nucleic acid sequence aberrations refer to rearrangements between and within nucleic acids, particularly chromosomal rearrangements. Nucleic acid sequence aberrations also refer to the deletion of a nucleic acid sequence, particularly chromosome deletions. As used herein, the term "nucleic acids" refers to both DNA and RNA.

A chromosome translocation is an example of a nucleic acid sequence aberration. A chromosome translocation refers to the movement of a portion of one chromosome to another chromosome (inter-chromosome rearrangement) as well the movement of a portion of a chromosome to a different location on that chromosome (intra-chromosome rearrangement). In general, chromosome translocations are characterized by the presence of a DNA sequence on a particular chromosome that is known to be native to a different chromosome or different portion of the same chromosome.

Chromosome translocations are frequently random genetic events which can occur at virtually any portion of any chromosome. Because the particular nucleic acid sequences involved in a chromosome translocation is not always known, it is generally not possible to design a hybridization probe that will uniquely identify a translocated sequence without first determining the translocated sequence. In addition, because chromosome translocations involve the movement of a nucleic acid sequence within a sample as opposed to the appearance or disappearance of the nucleic acid sequence, it generally is not possible to detect a chromosome translocation merely by assaying for the presence or absence of a particular nucleic acid sequence.

Chromosome translocations are known to be involved in carcinogenesis and inherited genetic disorders and have been shown to increase in frequency upon exposure to radiation and certain chemicals. Measurement of the frequency of chromosome translocations after exposure to radiation or a particular agent is therefore useful for evaluating the tendency of particular agents or forms of radiation to cause or increase the frequency of chromosome translocations.

Chromosome translocations are also known to be associated with specific diseases, including, for example lymphomas and leukemias, such as Burkitt's lymphoma, chronic myelocytic leukemia, chronic lymphocytic leukemia and granulocytic leukemia, as well as solid tumors such as malignant melanoma, prostate cancer and cervical cancer. A method for rapidly detecting a translocation associated with a disease is needed as a method for diagnosing disease.

Fluorescence in situ hybridization (FISH) using chromosome-specific composite hybridization probes ("chromosome painting") was developed as an assay for detecting chromosome translocations. FISH is described in Pinkel, et al., *Proc. Natl. Acad. Sci. (USA)* 83:2934–2938 (1986); Lucas, et al., *International Journal of Radiation Biology* 56:35–44 (1989), 62: 53–63 (1992); Pinkel, et al., *Proc. Natl. Acad. Sci. (USA)* 85:9138–9142 (1988), each of which is incorporated herein by reference.

The fluorescent hybridization probes used in FISH-based chromosome painting are chromosome-specific but not unique, i.e., they hybridize primarily to a particular chromosome type. Chromosome translocations are identified in the FISH assay by visually scanning individual cells for the presence of two different fluorescent signals on a single chromosome, the two fluorescent signals originating from two different FISH probes, each probe having homology to a different chromosome type.

Because each FISH probe hybridizes to a specific chromosome type and not to the chromosome translocation itself, it is not possible to determine the frequency of chromosome translocations directly from the fluorescence signal emanating from a FISH probe. Rather, the frequency of random chromosome translocations in a cell sample must be determined according to FISH assays by visually scanning individual cells. The need to visually scan individual cells effectively limits the number of cells that can be assayed, thereby reducing the sensitivity of the FISH assay and introducing the possibility of human error. A faster, more accurate method for quantifying chromosome translocations and other nucleic acid sequence aberrations is needed.

SUMMARY OF THE INVENTION

The present invention relates to a method for detecting nucleic acid sequence aberrations. As used herein, nucleic acid sequence aberrations refer to rearrangements between and within nucleic acid sequences, particularly chromosomes. Nucleic acid sequence aberrations also refer to the deletion of a nucleic acid sequence, particularly chromosome deletions. As used herein, the term "nucleic acids" refers to both DNA and RNA of any origin.

According to the method of the present invention, a nucleic acid sequence aberration is detected by detecting nucleic acid sequences having both a first nucleic acid sequence type (e.g., from a first chromosome) and a second nucleic acid sequence type (e.g., from a second chromosome), the presence of the first and the second nucleic acid sequence type on the same nucleic acid sequence indicating the presence of a nucleic acid sequence aberration. More specifically, a solution containing a sample of nucleic acids is contacted with a first and a second hybridization probe under conditions favorable for hybridization. The first hybridization probe includes a nucleic acid sequence that is at least partially complementary to a first nucleic acid sequence type. The first hybridization probe also includes a first complexing agent capable of attaching to a second complexing agent.

The second hybridization probe contains a nucleic acid sequence that is at least partially complementary to a second nucleic acid sequence type and that selectively hybridizes to the second nucleic acid sequence type over the first nucleic acid sequence type. The second hybridization probe also contains a detectable marker which enables the second hybridization probe to be detected.

The sample of nucleic acids is contacted with the second hybridization probe under conditions favorable for hybridization either before, after or during the hybridization of the first hybridization probe with the sample of nucleic acids.

The first complexing agent on the first hybridization probe is contacted with the second complexing agent bound to a solid support either before or after the first and/or second hybridization probe is hybridized to the sample of nucleic acids. By contacting the first and second complexing agents, the first hybridization probe becomes immobilized on the solid support. This enables the immobilization of any nucleic acid sequence hybridized to the first hybridization probe, i.e., a nucleic acid sequence that includes a nucleic acid sequence of the first type. The solid support also enables nucleic acid sequences hybridized to the first hybridization probe to be separated from nucleic acid sequences that do not hybridize to the first hybridization probe.

Once the sample of nucleic acid sequences are hybridized to the first and second hybridization probes and immobilized on to the solid support by the second complexing agent, the immobilized hybridized nucleic acid sequences are separated from any non-hybridized nucleic acid sequences and any non-hybridized second hybridization probes.

Only nucleic acid sequences containing the first nucleic acid sequence type, i.e. nucleic acid sequences which hybridize to the first hybridization probe, will be immobilized. Of these sequences, only nucleic acid sequences containing the second nucleic acid sequence type will hybridize to the second hybridization probe. Thus, after the separation step, the amount of immobilized second hybridization probe, measurable using the detectable marker, is directly proportional to the number of nucleic acid aberrations present in the sample of nucleic acids analyzed.

The detectable marker may be detected without separating the detectable marker from the solid support, for example by using $^{14}C$ as the detectable marker and using accelerator mass spectroscopy to detect the $^{14}C$ marker. Alternatively, the detectable marker may be separated from the solid support prior to detection. This may be accomplished by digestion of the immobilized nucleic acids, by dehybridizing the first and/or second hybridization probe or by detaching the first and second complexing agents. Alternatively, a detachable linker may be incorporated between the solid support and second complexing agent, the first hybridization probe and first complexing agent or the second hybridization probe and the detectable marker to enable the detectable marker to be detached from the solid support.

The method of the present invention increases by several fold the sensitivity, precision and speed of detecting randomly occurring nucleic acid sequence aberrations such as chromosome translocations over current detection methods including FISH assays. Thus, the method of the present invention is useful for evaluating clastogentic agents, such as radiation and certain chemicals, for their tendency to increase the frequency of nucleic acid sequence aberrations.

The method of the present invention may also be readily adapted for the diagnosis of disease, the occurrence of which is associated with and/or identifiable by the presence of a particular nucleic acid sequence aberration. According to this embodiment of the method, the first and second hybridization probes are designed to selectively hybridize to a first and a second nucleic acid sequence type, the nucleic acid sequence aberration of which is associated with and/or characteristic of a disease.

Only nucleic acid sequences containing both the first and second nucleic acid sequence types, the aberration of which is associated with and/or characteristic of a disease, will hybridize to both the first and second hybridization probes. As a result, the detection of the second hybridization probe immobilized on the solid support may be used to diagnose a disease associated with the particular nucleic acid aberration being detected.

The present invention also relates to a kit for detecting nucleic acid aberrations and diagnosing disease according to the methods of the present invention. In general, the kits of the present invention include a first hybridization probe, and a second hybridization probe as described herein. The kits may also include a second complexing agent bound to a solid support as described herein as well as instructions for using the kit.

BRIEF DESCRIPTION OF THE DRAWINGS

FIGS. 1, 2 and 3 A–G depict an exemplary method of the present invention for detecting a chromosome translocation.

FIG. 1 depicts the hybridization of the first and second hybridization probes to a sample of chromosomal DNA, a fragment of which contains a translocation.

FIG. 2 depicts the immobilization of the hybridized chromosomal DNA to a solid support and the separation of the immobilized DNA from non-immobilized DNA.

FIGS. 3A-G depict several approaches to isolating and/or detecting the detectable marker on the immobilized second hybridization probe.

FIG. 3A illustrates the detectable marker being detected by first digesting the nucleic acids immobilized on the solid support using DNase.

FIG. 3B illustrates the detectable marker being separated from the solid support prior to detection of the detectable marker by the dehybridization of the first hybridization probe.

FIG. 3C illustrates the detectable marker being separated from the solid support prior to detection of the detectable marker by the dehybridization of the second hybridization probe.

FIG. 3D illustrates the detectable marker being separated from the solid support prior to detection of the detectable marker by detaching the second complexing agent from the solid support.

FIG. 3E illustrates the detectable marker being separated from the solid support prior to detection of the detectable marker by detaching the first and second complexing agents.

FIG. 3F illustrates the detectable marker being separated from the solid support prior to detection of the detectable marker by detaching the first complexing agent from the first hybridization probe.

FIG. 3G illustrates the detectable marker being separated from the solid support prior to detection of the detectable marker by detaching the detectable marker from the second hybridization probe.

FIGS. 4A and 4B illustrate the detection of the Philadelphia chromosome wherein FIG. 4A illustrates the use of a second hybridization probe specific for the abl gene and FIG. 4B illustrates the use of a composite second hybridization probe for chromosome 9.

DETAILED DESCRIPTION OF THE INVENTION

Figure 1:
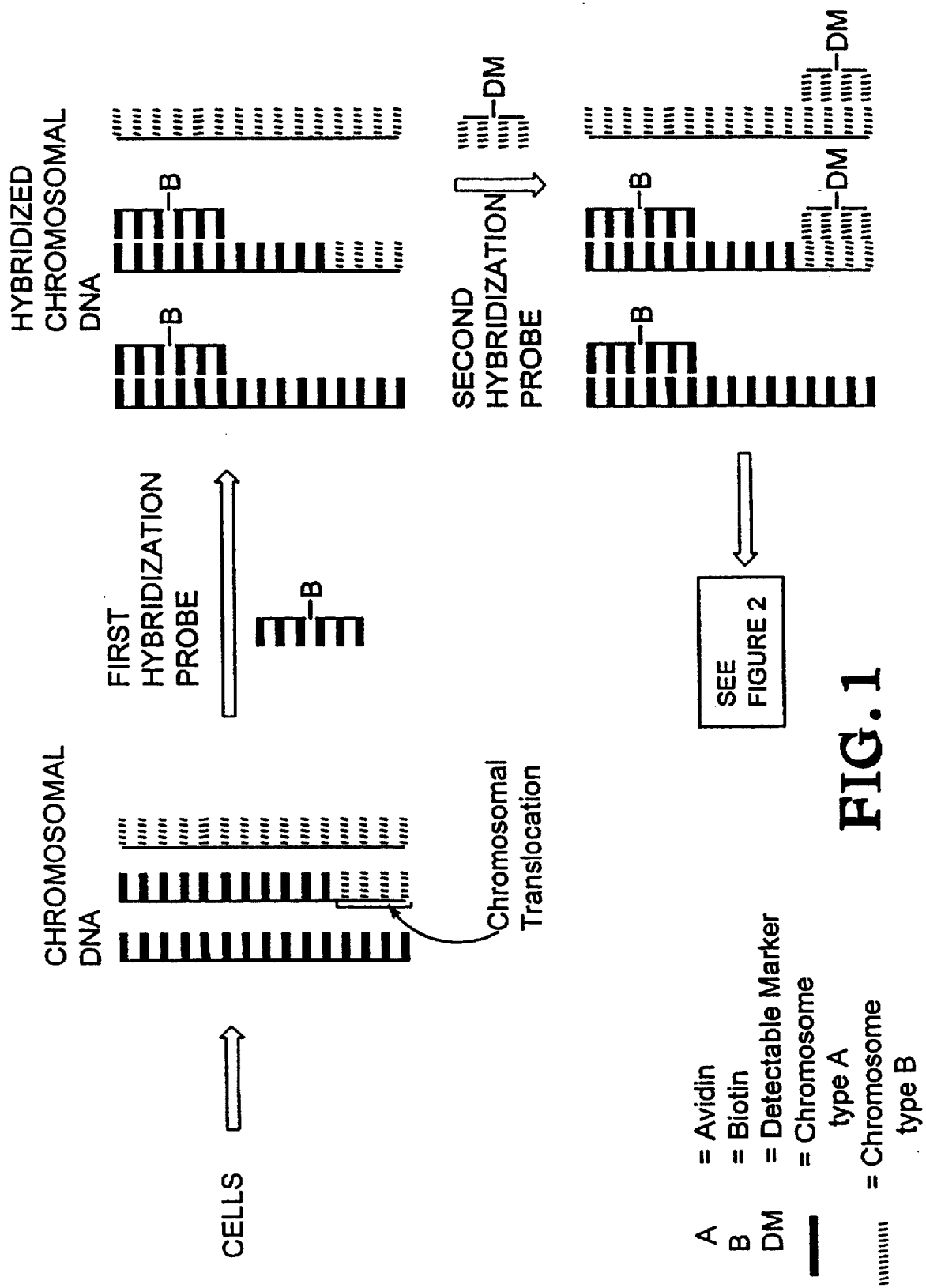

The present invention relates to a rapid and efficient method for detecting nucleic acid sequence aberrations using hybridization probes. Unlike the FISH assay which requires visually scanning individual cells, the method of the present invention is designed to enable the use of a detectable marker to analytically quantify the frequency of nucleic acid sequence aberrations such as chromosome translocations. Because an analytically detectable marker is used to measure nucleic acid sequence aberrations rather than visually scanning individual cells, one is able to analyze over a thousand times as many cells for aberrations than was previously possible using the FISH assay. This large increase in the number of cells that may be analyzed at a time significantly enhances the speed, sensitivity and accuracy of nucleic acid sequence aberration detection. For example, it would permit the measurement of nucleic acid sequence aberrations in large populations evaluated epidemiologically. This is not possible using the current FISH technology.

The present invention also relates to the diagnosis of diseases, such as cancer and genetic disorders, which are associated with and/or identifiable by the presence of a particular nucleic acid sequence aberration. For example, the translocation of oncogene c-myc, which is normally located on chromosome 8q to chromosome 14, referred to as a t(8;14) translocation, is characteristic of Burkitt's lymphoma. Using the method of the present invention for detecting aberrations, diseases such as Burkitt's lymphoma may be readily diagnosed. Further, given the large number of cells that can be evaluated using the present method, very low translocation frequencies can be measured. Thus, the method of the present invention represents a valuable tool for the early detection of disease.

Examples of diseases that may be detected according to the method of the present invention include, but are not limited to lymphomas and leukemias, such as Burkitt's lymphoma which is identifiable by a unique translocation between chromosomes 8 and 14, chronic myelogenous leukemia which is identifiable by a unique translocation between chromosomes 9 and 22, chronic lymphocytic leukemia which is identifiable by a unique translocation between chromosomes 11 and 14 and granulocytic leukemia which involves granulocytes which cannot be cultured, t(8;21). Detection of such specific translocations may also be helpful in evaluation the progression of AIDS. Unique translocations may also be identified in solid tumors, such as, malignant melanoma, t(1: 19)(q12: q13), prostate cancer t(8:12) and cervical cancer, t(1,8)(q22:p23.1) and t(1:5) (q25:p32). Further, as new diseases are linked to the occurrence of a nucleic acid sequence aberration, these new diseases will also be rapidly detectable using the method of the present invention.

Using the method of the present invention, diseased cells, such as cancer cells can be rapidly detected. Further, because a relatively large number of cells can be assayed at a time with a high level of sensitivity, the method of the present invention provides an effective tool for detecting these diseases at an early stage when treatment of these diseases is most likely to be effective.

The present invention also relates to a kit for detecting nucleic acid aberrations and diagnosing disease according to the methods of the present invention. In general, the kits of the present invention include a first hybridization probe and a second hybridization probe as described herein. The kits may also include a second complexing agent bound to a solid support as described herein. Optionally, the kits may also include instructions describing how to use the kit to detect nucleic acid sequence aberrations and the diagnosis of disease associated with or identifiable by the presence of a particular nucleic acid sequence aberration.

Specific examples of disease diagnosis kits that may be prepared according to the present invention include kits for diagnosing malignancies such as Burkitt's lymphoma, chronic myelocytic leukemia, chronic lymphocytic leukemia, granulocytic leukemia, malignant melanoma, prostate cancer, and cervical cancer.

According to the method of the present invention, a sample of nucleic acids is first obtained. As illustrated in FIG. 1, in applications where the nucleic acid sample consists of chromosomal DNA, the chromosomal DNA is first isolated from a sample of cells. Chromosomal DNA may be isolated by any of the variety of methods known in the art. For example, the chromosomal DNA may be isolated by the method taught in Vooijs, et al. *Am. J. Hum. Genet.* 52:586-597 (1993) or by using the GIBCO BRL TRIzol™ Reagent (Life Technologies, Gaithersburg, MD), each of which is incorporated herein by reference.

Chromosomal DNA may be analyzed as whole chromosomes, chromosome fragments or chromosomal DNA fragments, all of which are hereinafter referred to as chromosomal DNA. When analyzing chromosomal DNA for the presence of nucleic acid sequence aberrations, the chromosomal DNA may be organized as an extended double strand, as extended nucleosomes, as chromatin fiber, as folded fiber, and as interphase, prophase or metaphase DNA. Sandberg,"The chromosomes in human cancer and leukemia", Elsevier; New York (1980), pp. 69–73.

The preferred chromosome organization for assaying chromosomal DNA for the presence of a nucleic acid sequence aberration depends on the number of nucleic acid bases separating the first and second nucleic acid sequence types being recognized by the first and second hybridization probes to identify the aberration. The preferred size of the solid support, if a particulate solid support such as beads are employed, is a function of the size of the piece of target DNA or RNA to be evaluated. For example, target pieces of DNA can range from less than a micron to several millimeters in length depending on the level of organization used and the degree to which the chromosomes are fractionated. For example, detection of the Philadelphia chromosome would require target pieces on the order of a few hundred kilobases (less than 1 mm) if the DNA molecules are fully extended and only a few microns if the chromosomes are in the interphase level of organization.

As illustrated in FIG. 1, once the sample of nucleic acids is obtained, the nucleic acid sample is contacted with a first hybridization probe under conditions favorable for hybridization. The first hybridization probe is specific for a first nucleic acid sequence type, i.e., it is at least partially complementary to the first nucleic acid sequence type and therefore selectivity hybridizes to that nucleic acid sequence type.

In the case of detecting chromosomal translocations, the first hybridization probe is preferably a chromosome-specific probe such that it selectivity hybridizes to a particular chromosome type. In the case of detecting interchromosomal rearrangements,"chromosome type" refers to individual chromosomes. In the case of detecting intrachromosomal rearrangements,"chromosome type" refers to different portions of an individual chromosome since intrachromosomal rearrangements involve the movement of a sequence to a different portion of the same chromosome.

Any hybridization probe which preferentially hybridizes to a particular nucleic acid sequence may be used as the first hybridization probe and is intended to fall within the scope of the present invention. In the case of detecting chromosome translocations, an exemplary method for preparing PCR libraries of individual chromosomes and the use of those libraries to prepare chromosome-specific hybridization probes is taught in Vooijs, et al. *Am. J. Hum. Genet.* 52:586–597 (1993) which is incorporated herein by reference.

Because the first hybridization probe is selective for a first nucleic acid sequence type as opposed to the nucleic acid sequence aberration itself, the first hybridization probe hybridizes to all nucleic acid sequences containing the first nucleic acid sequence type. For example, with regard to detecting chromosome translocations, the first hybridization probe may be a chromosome specific probe. Thus, the first hybridization probe does not by itself detect the nucleic acid sequence aberration. Rather, the method of the present invention relies upon the second hybridization probe to identify those nucleic acid sequences isolated by the first hybridization probe which also has a nucleic acid sequence of a second type. By contrast, in most prior art hybridization assays using two hybridization probes, the first hybridization probe selectively isolates the nucleic acid being detected while the second hybridization probe serves to enable detection of the nucleic acid sequence isolated by the first hybridization probe.

The first hybridization probe also includes a first complexing agent that is capable of forming a binding pair with a second complexing agent. The second complexing agent is attached to a solid support, thereby enabling the immobilization of the first hybridization probe on the solid support.

The first and second complexing agents used to attach the first hybridization probe to the solid support may be any pair of complexing agents which form a strong binding pair. Since elevated temperatures are generally required for hybridization, the binding pair should preferably be stable at temperatures at least up to about 37° C.

Examples of suitable binding pairs of complexing agents include antibody-antigen pairs, biotin-avidin and digoxigenin-anti-digoxigenin. Avidin-biotin and analogues and derivatives thereof are particularly preferred as binding pairs due to their enhanced thermal stability. Examples of avidin derivatives include, but are not limited to, streptavidin, succinyl avidin, ferritin avidin, enzyme avidin and cross-linked avidin. Examples of biotin derivatives include, but are not limited to caproylamidobiotin and biocytin. Examples of biotin analogues include, but are not limited to desthiobiotin and biotin sulfone. Biotin-antibiotin antibody is an example of a suitable antibody-antigen pair.

Any solid support to which a complexing agent may be attached may be used in the present invention. Examples of suitable solid support materials include, but are not limited to, silicates such as glass and silica gel, cellulose and nitrocellulose papers, nylon, polystyrene, polymethacrylate, latex, rubber, and fluorocarbon resins such as TEFLON™.

The solid support material may be used in a wide variety of shapes including, but not limited to slides and beads. Slides provide several functional advantages and thus are a preferred form of solid support. Slides can be readily used with any chromosome organization. Due to their flat surface, probe and hybridization reagents can be minimized using glass slides. Slides also enable the targeted application of reagents, are easy to keep at a constant temperature, are easy to wash and facilitate the direct visualization of DNA immobilized on the solid support. Removal of DNA immobilized on the solid support is also facilitated using slides. It is estimated that a standard microscope glass slide can contain 50,000 to 100,000 cells worth of DNA. Beads, such as BioMag® Strepavidin magnetic beads are another preferred form of solid support containing a second complexing agent.

It is preferred that avidin or an avidin derivative be used as the second complexing agent. Avidin may be chemically attached to glass using the N-hydroxysuccinamide active ester of avidin as taught by Manning, et al. *Biochemistry* 16:1364–1370 (1977) and may be attached to nylon by a carbodiimide coupling as taught by Jasiewicz, et al. *Exp. Cell Res.* 100:213–217 (1976). Magnetic microbeads labelled with avidin and strepavidin labelled bead may be obtained from Advanced Magnetics, Inc., Cambridge, MA and from Spherotech, Inc., Libertyville, IL.

The first hybridization probe may be immobilized on to the solid support either before or after the first hybridization probe is hybridized to the sample of nucleic acids. The first hybridization probe is preferably attached to the solid support after the probe is hybridized to the sample of nucleic acids since it is believed that hybridization is impeded when the probe is attached to the solid support.

Once nucleic acids of a first nucleic acid sequence type have been hybridized to the first hybridization probe and immobilized on the solid support, the hybridized nucleic acids may be separated from any non-hybridized nucleic acids. Separation of the hybridized nucleic acids from non-hybridized nucleic acids may be accomplished by a variety of methods known in the art including, but not limited to, centrifugation, filtration and washing.

Once any non-hybridized nucleic acids have been removed, the immobilized hybridized nucleic acids are then contacted with a second hybridization probe under conditions favorable for hybridization.

Figure 2:
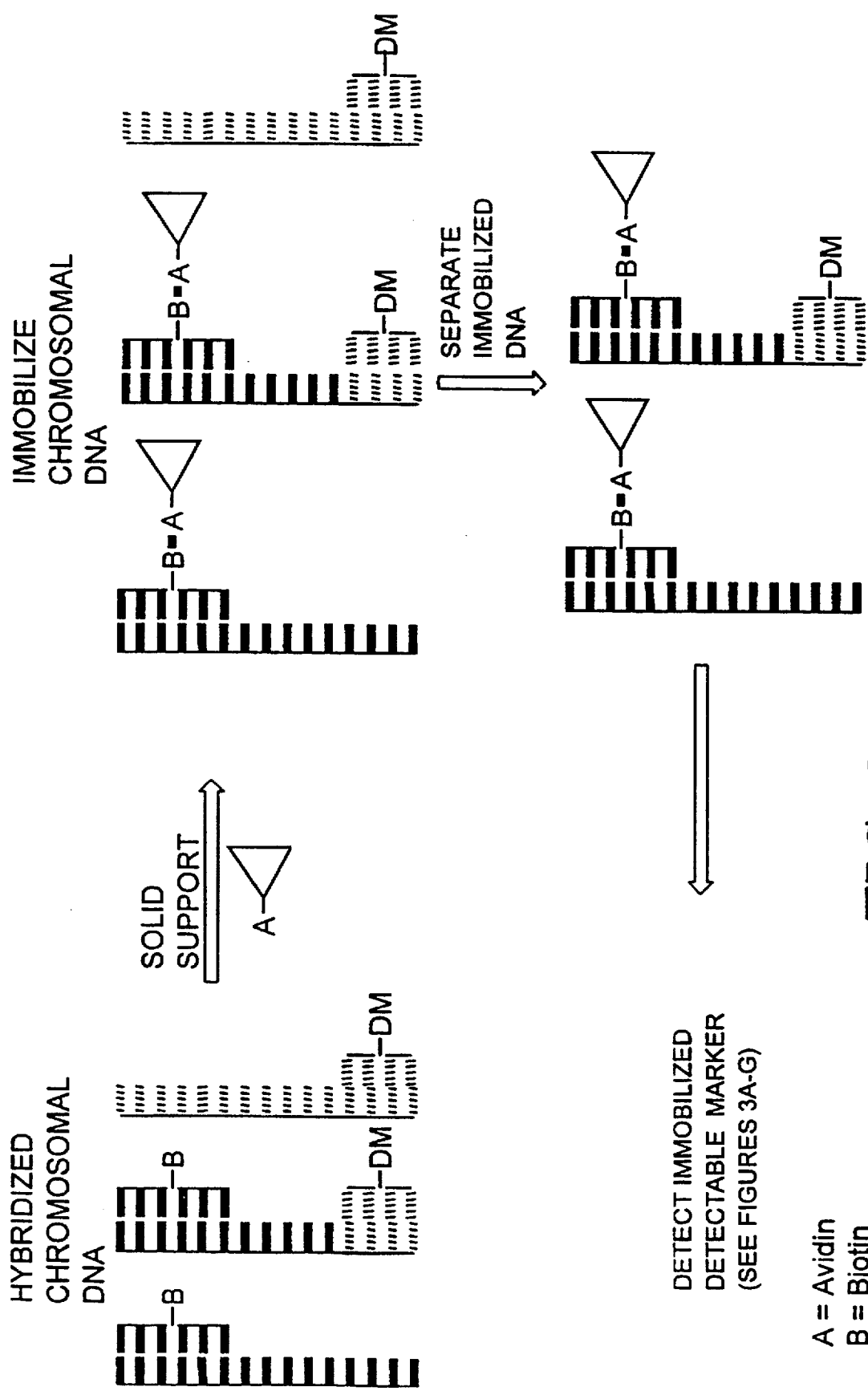

Optionally, the second hybridization probe may be contacted with the nucleic acid sample before or simultaneously with the hybridization of the first hybridization probe to the nucleic acid sample. FIGS. 1 and 2 illustrate the second hybridization probe being hybridized to the chromosomal DNA prior to immobilizing the hybridized chromosomal DNA on the solid support.

It is preferred that the second hybridization probe be used after the first hybridization and immobilization in order to enable nucleic acids of the second type that do not contain a nucleic acid sequence of the first type to be eliminated through a separation step. By eliminating nucleic acid sequences of the second chromosome type that do not also contain a nucleic acid sequence of the first type prior to introducing the second hybridization probe, less nucleic acids sequences are present which can nonspecifically bind to the second hybridization probe. In addition, less second hybridization probe is needed. Both of these factors aid in minimizing the amount of second hybridization probe that becomes immobilized that is not bound to a nucleic acid sequence aberration. This serves to minimize the amount of background noise present in the assay, thereby enabling greater assay accuracy and lower detection limits.

The second hybridization probe includes a nucleic acid sequence that does not hybridize to nucleic acids of the same type as the first hybridization probe. Any nucleic acid sequence which does not hybridize to the first nucleic acid sequence type may be used in the second hybridization probe and is intended to fall within the scope of the present invention. The second hybridization probe further includes an analytically detectable marker which is used to quantify the frequency of the nucleic acid sequence aberration being detected.

When detecting random nucleic acid sequence aberrations, such as random chromosomal translocations, the second hybridization probe preferably is a composite chromosome hybridization probe capable of hybridizing along the entire length of a chromosome other than the chromosome to which the first hybridization probe hybridizes. By using a composite hybridization probe, multiple second hybridization probes may be used to complete the identification of the nucleic acid sequence aberration. By having multiple second hybridization probes bind to the target sequence, the signal generated by the detectable marker can be amplified thereby increasing the sensitivity of the method. The use of a composite hybridization probe as the second hybridization probe is described in Example 1 and illustrated in FIGS. 4A and 4B.

Optionally, the second hybridization probe may hybridize to more than one chromosome type other than the chromosome type to which the first hybridization probe hybridizes. In this embodiment, the second hybridization probe enables the rapid identification of all nucleic acid sequence aberrations involving the chromosome identified by the first hybridization probe.

Where possible, the second hybridization probe preferably includes a nucleic acid sequence that is uniquely specific to the nucleic acid sequence aberration being detected. The use of uniquely specific hybridization sequences is preferred since it minimizes the occurrence of background noise due to non-specific binding. For example, when detecting particular nucleic acid sequence aberrations, the second hybridization probe is preferably specific for a particular nucleic acid sequence. For example, some diseases, such as cancer and genetic disorders appear to arise from a specific chromosome translocation. By using a second probe that is specific for a nucleic acid sequence, the translocation of which is associated with a particular disease, it is possible to rapidly identify the presence of chromosome translocations associated with the disease to be diagnosed. It is also preferred to employ a composite second hybridization probe which includes a series of sequences that are all either unique or chromosome specific for the aberration being detected.

According to the method of the present invention, the first hybridization step and the immobilization step enables the separation of nucleic acid sequences of a first nucleic acid sequence type. Since the second hybridization probe is designed so that it does not hybridize to nucleic acid sequences of the first nucleic acid type, the second hybridization probe does not bind to nucleic acids immobilized by the first hybridization probe that do not contain a nucleic acid sequence aberration. As a result, the amount of detectable marker detected due to the hybridization of the second hybridization probe to the immobilized nucleic acids is directly proportional to the frequency of nucleic acid sequence aberration in the sample of nucleic acids being analyzed.

Non-specific binding by the non-unique first and second hybridization probes to the nucleic acid sample may be minimized through the use of suppression techniques such as is disclosed by Pinkel, et al. *Proc. Natl. Acad. Sci. USA* (1988) 85:9138–9142 which is incorporated herein by reference. As taught in Pinkel, et al. unlabelled nucleic acid probes, for example, unlabelled genomic DNA, may be used to competitively inhibit non-specific hybridization.

The first and second hybridization probes may include RNA or DNA sequences such that the complementary nucleic acid sequences formed between the hybridization probes and the target sequence may be two DNA sequences or a RNA and a DNA sequence.

Any analytically detectable marker that can be attached to or incorporated into a hybridization probe may be used in the present invention. An analytically detectable marker refers to any molecule, moiety or atom which can be analytically detected and quantified. Methods for detecting analytically detectable markers include, but are not limited to, radioactivity, fluorescence, absorbance, mass spectroscopy, EPR, NMR, XRF, luminescence and phosphorescence. For example, any radiolabel which provides an adequate signal and a sufficient half-life may be used as a detectable marker. Commonly used radioisotopes include $^3$H, $^{14}$C, $^{32}$P and $^{125}$I. In a preferred embodiment, $^{14}$C is used as the detectable marker and is detected by accelerator mass spectroscopy (AMS). $^{14}$C is preferred because of its exceptionally long half-life and because of the very high sensitivity of AMS for detecting $^{14}$C isotopes. Other isotopes that may be detected using AMS include, but are not limited to, $^3$H, $^{125}$I, $^{41}$Ca, $^{63}$Ni and $^{36}$Cl.

Fluorescent molecules, such as fluorescein and its derivatives, rhodamine and its derivatives, dansyl, umbeliferone and acridimium, and chemiluminescent molecules such as luciferin and 2,3-dihydrophthalazinediones may also be used as detectable markers. Molecules which bind to an analytically detectable marker may also be covalently attached to or incorporated into hybridization probe, for example, as taught by Ward, European Patent Application No. 63,879 which is incorporated herein by reference. In such instances, the hybridization probe is detected by adding an analytically detectable marker which specifically binds to the probe, thereby enabling detection of the probe. Examples of such molecules and their analytically detectable counterparts include biotin and either fluorescent or chemiluminescent avidin. Antibodies that bind to an analytically detectable antigen may also be used as a detectable marker. The detectable marker may also be a molecule which, when subjected to chemical or enzymatic modification, becomes analytically detectable such as those disclosed in Leary, et al., *Proc. Natl. Acad. Sci. (U.S.A.)*, 80:4045–4049 (1983) which is incorporated herein by reference. Other examples of suitable detectable markers include protein binding sequences which can be detected by binding proteins, such as those disclosed in U.S. Pat. No. 4,556,643 which is incorporated herein by reference.

As discussed herein, the nucleic acid sequence employed in the second hybridization probe may itself function as a detectable marker where the bases forming the nucleic acid sequence are quantified using techniques known in the art.

Once the nucleic acid sequences containing the first nucleic acid sequence type are hybridized to the first and second hybridization probes and immobilized on to the solid support by the second complexing agent, the immobilized hybridized nucleic acid sequences are separated from any non-hybridized nucleic acid sequences and any non-hybridized second hybridization probes. Since nucleic acid sequence aberrations are detected and quantified based on the presence or absence of the detectable marker attached to a second hybridization probe, it is critical that any second hybridization probe containing the detectable marker that is not hybridized to the nucleic acid sample be removed. Removal of nucleic acids that are not hybridized to the solid support may be readily performed by a variety of separation techniques known in the art including centrifugation, filtration and washing.

Once any nucleic acids and hybridization probes that are not immobilized to the solid support have been removed, the presence or absence of the detectable marker attached to the second hybridization probe is detected in order to detect the presence or absence of a nucleic acid aberration. As discussed above, the second hybridization probe will only be immobilized onto the solid support if the nucleic acid to which the second hybridization probe is hybridized contains a detectable marker.

The detection and quantification of the detectable marker can be performed using a variety of methods, depending upon the particular hybridization probes and detectable markers employed.

Figure 3A:
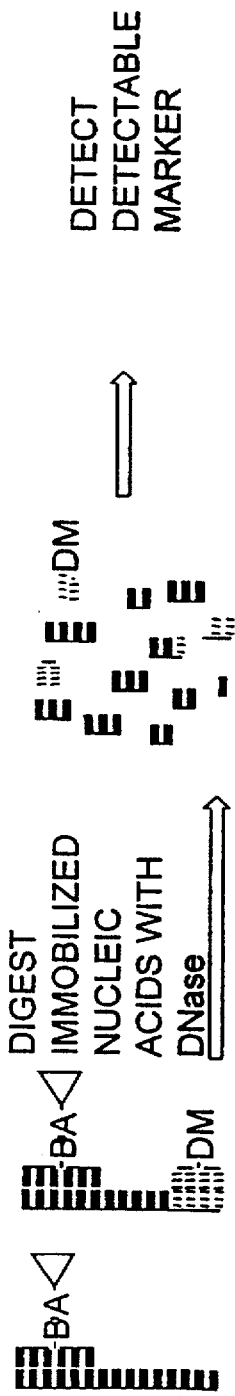

In one embodiment, illustrated in FIG. 3A, the detectable marker is detected by treating the immobilized nucleic acid sequences with DNase to digest any DNA immobilized on the solid support. The digested DNA is then collected after enzymatic digestion and analyzed for the presence of the detectable marker. Alternatively, the nucleic acids attached to the solid support may be removed from the solid support by a variety of chemical and physical methods available, including, for example, treatment with a basic solution (e.g., concentrated NaOH), treatment with an acidic solution and denaturalization of DNA using standard methods such as elevated temperatures or reagents. For example, when the detectable marker used is $^{14}C$, the entire solid support containing the immobilized nucleic acids and hybridization probes may be graphitized and analyzed using accelerator mass spectroscopy (AMS). The use of AMS and a $^{14}C$ detectable marker to quantify nucleic acid aberrations is described in greater detail in Example 1.

Figure 3B:
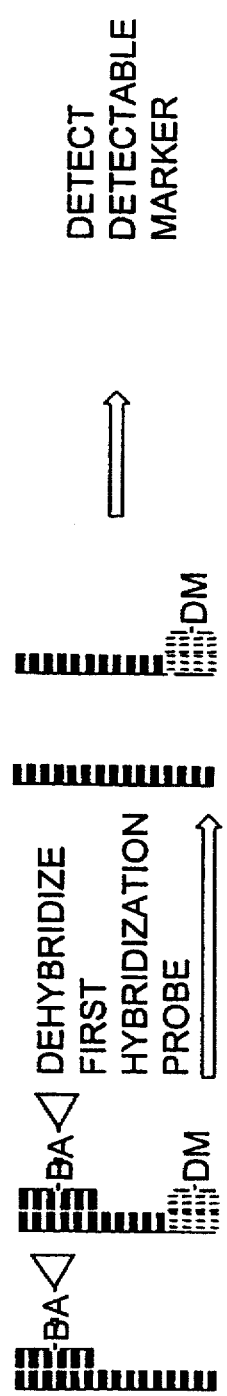
Figure 3C:
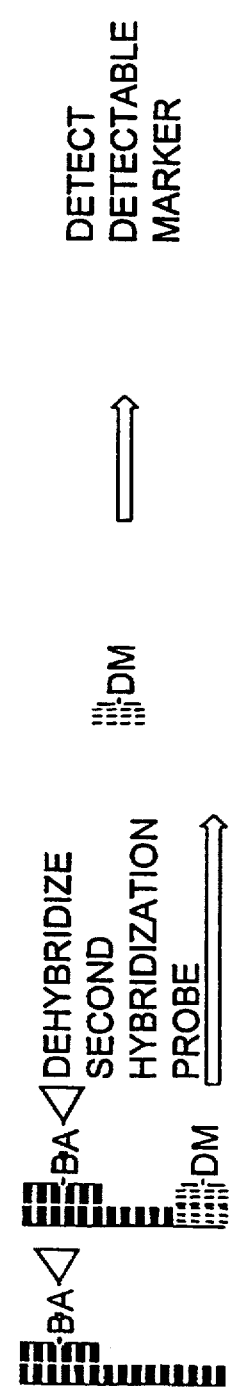

In another embodiment, illustrated in FIGS. 3B and 3C, the detectable marker is separated from the solid support prior to detection of the detectable marker by dehybridizing the first and/or the second hybridization probe to the target nucleic acid sequence. This may be done by heating the solid support and immobilized sequences to at least 70° C.

By controlling the length of the nucleic acid sequences forming the first and/or second hybridization probes it is possible to selectively dehybridize the first and second hybridization probes in a particular order. It is also possible to selectively dehybridize the first and second hybridization probes in a particular order by biotinylating one of the hybridization probes and incorporating digoxigenin onto the other hybridization probe. It has been observed that biotinylated probes dehybridize at a lower temperature than hybridization probes containing digoxigenin.

Chromosomal DNA immobilized on the solid support tends to become entangled with one or more strands of chromosomal DNA as well as the solid support. In addition, chromosomal DNA is generally immobilized on the solid support at multiple sites. It is therefore generally preferred to dehybridize the second hybridization probe selectively over the first hybridization probe. When the second hybridization probe is selectively dehybridized over the first hybridization probe, the nucleic acids forming the second hybridization probe may be quantified and thus used as the detectable marker. Quantification of the nucleic acids may be performed by a variety of methods known in the art, preferably by measuring the absorbance of the nucleic acids using UV spectroscopy, or by quantitative commercial calorimetric methods (e.g. the "DNA DIPSTICK" sold by Invitrogen, San Diego, CA).

Selectively dehybridizing the first hybridization probe over the second hybridization probe is desirable in instances where it is sought to isolate nucleic acid containing the nucleic acid sequence aberration. Selectively dehybridizing the second hybridization probe over the first hybridization probe is desirable in instances where it is sought to isolate only the second hybridization probe, for example, in order to use the nucleic acids of the second hybridization probe as a detectable marker. Selectively dehybridizing the second hybridization probe is also desirable where it is sought to maintain the target sequence immobilized onto the solid support in order employ a different second hybridization probe on the same sample of nucleic acids. For example, one might wish to assay for a chromosome translocation between chromosome 1 and chromosomes 2–5. Thus, by being able to selectively dehybridize the second hybridization probe, it is possible to immobilize chromosome 1 using a first hybridization probe and then sequentially assay for translocations between chromosome 1 and chromosomes 2–5 using a series of different second hybridization probes.

In another embodiment, illustrated in FIG. 3D, the detectable marker is separated from the solid support prior to detection of the detectable marker by breaking the bond between the second complexing agent and the solid support. This may be accomplished through the use of a detachable linker positioned between the second complexing agent and the solid support. Examples of suitable detachable linkages include, but are not limited to the detachable linkers described in Lin, et al., *J. Org. Chem.* 56:6850–6856 (1991); Ph.D. Thesis of W.-C. Lin, U.C. Riverside, (1990); Hobart, et al., *J. Immunological Methods* 153: 93–98 (1992); Jayabaskaran, et al., *Preparative Biochemistry* 17(2): 121–141 (1987); Mouton, et al., *Archives of Biochemistry and Biophysics* 218: 101–108 (1982); Funkakoshi, et al., *J. of Chromatography* 638:21–27 (1993); Gildea, et al., *Tetrahedron Letters* 31: 7095–7098 (1990); and WO 85/04674, each of which are incorporated herein by reference.

In another embodiment, illustrated in FIG. 3E, the detectable marker is separated from the solid support prior to detection of the detectable marker by breaking the bond between the first and second complexing agents. For example, using antidigoxigenin and digoxigenin as the first and second binding agents, the bond between the first and second complexing agents may be broken.

In another embodiment, illustrated in FIG. 3F, the detectable marker is separated from the solid support prior to detection of the detectable marker by breaking the bond between the first complexing agent and the nucleic acid sequence forming the first hybridization probe. This may be accomplished through the use of a detachable linker positioned between the first complexing agent and the nucleic acid sequence forming the first hybridization probe. Examples of suitable detachable linkages include, but are not limited to the detachable linkers described in the references cited above.

In yet another embodiment, illustrated in FIG. 3G, the detectable marker is separated from the solid support prior to detection by detaching the detectable marker from the second hybridization probe. This may be accomplished through the use of a detachable linker between the detectable marker and the second hybridization probe. Examples of suitable detachable linkages include, but are not limited to, the detachable linkers described in the references cited above.

The detectable marker may be detected by a variety of methods known in the art, depending on the particular detectable marker employed. For example, AMS may be used when the detectable marker is a radioisotope such as $^{14}C$, liquid scintillation may be used when the detectable marker is tritiated thymidine and standard fluorescence or spectroscopic methods may be used when the detectable marker is a fluorescent molecule or the DNA itself.

A nucleic acid sequence aberration frequency rate may be determined based on the signal generated from the detectable marker using a calibration curve. The calibration curve may be formed by analyzing a sample of cells having a known nucleic acid sequence aberration frequency rate. For example, a calibration curve for the nucleic acid sequence aberration may be generated by analyzing a series of known amounts of cells from a cell line in which the aberration rate of the cell line is known. Alternatively, samples of cells may be analyzed according to the method of the present invention and according to a method known in the art for quantifying a nucleic acid sequence aberration. For example, the FISH method for detecting chromosome translocations may be used to determine the nucleic acid sequence aberration frequency rate of a sample of cells. Then, by serially diluting the sample of cells and assaying the cells according to the method of the present invention, a calibration curve may be generated. Alternative methods for generating a calibration curve are within the level of skill in the art and may be used in conjunction with the method of the present invention.

When quantifying the frequency of chromosome translocations in a sample, it is preferred to correct the translocation frequency measured to account for the presence of dicentric chromosomes which can provide a false positive reading. Dicentric chromosomes include the chromosomal DNA from the two chromosomes making up the dicentric chromosome. As a result, depending on the particular hybridization probes used, dicentric chromosomes can be incorrectly measured as translocations.

Dicentric chromosomes are characterized by having two centromeres where each centromere is of a different chromosome type. Dicentric chromosomes may be identified according to the method of the present invention by employing first and second hybridization probes which each hybridize to the centromere of different chromosome. The dicentric chromosome frequency determined may be subtracted from the measured translocation frequency to provide the translocation frequency.

The following example sets forth a method for detecting a chromosome translocation associated with chronic myelogenous leukemia according to the method of the present invention. Further objectives and advantages of the present invention other than those set forth above will become apparent from the example which is not intended to limit the scope of the present invention.

EXAMPLE

1. Detection of a Chromosome Translocation

Chronic myelogenous leukemia (CML) is genetically characterized by the fusion of the bcr and abl genes on chromosomes 22 and 9 respectively to produce a cytogenetically distinct Philadelphia chromosome. In most cases, the fusion also involves a reciprocal translocation between chromosomes 9 and 22. This example provides a method for detecting cells having the distinctive Philadelphia chromosome indicating the presence of chronic myelogenous leukemia.

According to the method of the present invention, the first hybridization probe is formed using the 18-kb phage PEM12 probe (bcr probe) described in Tkachuk, et al., *Science* 250: 559–562 (1990) which is incorporated herein by reference. Copies of the first hybridization probe may be generated using pcr as described in Vooijs, et al., *Am. J. Hum. Genet.* 52: 586–597 (1993) and chemically modified to incorporate biotinylated uridine as the first complexing agent according to the method of Pinkel, et al., *Proc. Natl. Acad. Sci. (USA)* 83:2934–2938 (1986), each of which is incorporated herein by reference.

The second hybridization probe is formed using the 28-kb cosmid c-H-abl probe (abl probe) described in Tkachuk, et al. Copies of the second hybridization probe are generated using pcr as is described in Vooijs, et al., *Am. J. Hum. Genet.* 52: 586–597 (1993). A $^{14}C$ detectable marker is incorporated into the second hybridization probe by the introduction of $^{14}C$ labelled nucleotides using pcr.

Blood and bone marrow cells from a patient to be tested are isolated according to the procedure described in Tkachuk, et al. DNA from the cell sample is then isolated from the cells using standard methods such as those associated with using the GIBCO BRL TRIzOl™ Reagent (Life Technologies, Gaithersburg, MD), which is incorporated herein by reference. DNA from the cell sample may also be isolated by procedure described in Tkachuk, et al. The isolated DNA is fractionated into small pieces using restriction enzymes or other appropriate methods as described in Pinkel, et al., *Proc. Natl. Acad. Sci. (USA)* 83:2934–2938 (1986).

The first and second hybridization probes are hybridized to the fractionated DNA sample using the hybridization conditions described in Tkachuk, et al. Alternatively, the first and second hybridization probes may be hybridized to the fractionated DNA sample in separate steps.

Once the first and second hybridization probes have been hybridized to the sample of nucleic acids, solid support labelled with avidin is added to immobilize the first hybridization probe by an avidinbiotin linkage. Any nucleic acids hybridized to the first hybridization probe also become immobilized to the solid support. The avidin labelled solid support may be prepared by the methods described in Manning, et al. *Biochemistry* 16:1364–1370 (1977) and Jasiewicz, et al. *Exp. Cell Res.* 100:213–217 (1976), each of which are incorporated herein by reference.

The solid support is then washed with cold, pH 7 buffered saline to remove any first and second hybridization probes and DNA segments which are not immobilized on the solid support.

Once any non-hybridized second hybridization probe has been removed by the saline wash, the nucleic acids immobilized on the solid support are analyzed for the presence of $^{14}C$. DNase or concentrated NaOH is employed to separate any immobilized nucleic acids from the solid support. The nucleic acids isolated are then grafitized and analyzed using AMS for the presence of $^{14}C$ according to the method of Vogel et. al., *Anal. Chem.* 11: 142–149 (1991) which is incorporated herein by reference.

A nucleic acid sequence aberration frequency rate may be determined from the $^{14}C$ signal obtained from the accelerator mass spectrometer using a calibration curve. The calibration curve may be formed by analyzing a sample of cells having a known nucleic acid sequence aberration frequency rate. For example, a calibration curve for the nucleic acid sequence aberration associated with chronic myelogenous leukemia may be obtained by analyzing a series of known amounts of cells from the K-562 cell line which contain a reciprocal translocation between chromosome 9 and chromosome 22.

Alternatively, samples of cells may be analyzed according to the method of the present invention and according to a method known in the art for quantifying nucleic acid sequence aberrations. For example the FISH assay method described in Tkachuk, et al. may be used to determine the nucleic acid sequence aberration frequency rate of a sample of cells. Then, by serially diluting the sample of cells and assaying the cells according to the method described in the present example, a calibration curve may be generated. Alternative methods for generating a calibration curve are within the level of skill in the art and may be used in conjunction with the method of the present invention.

Figure 4B:
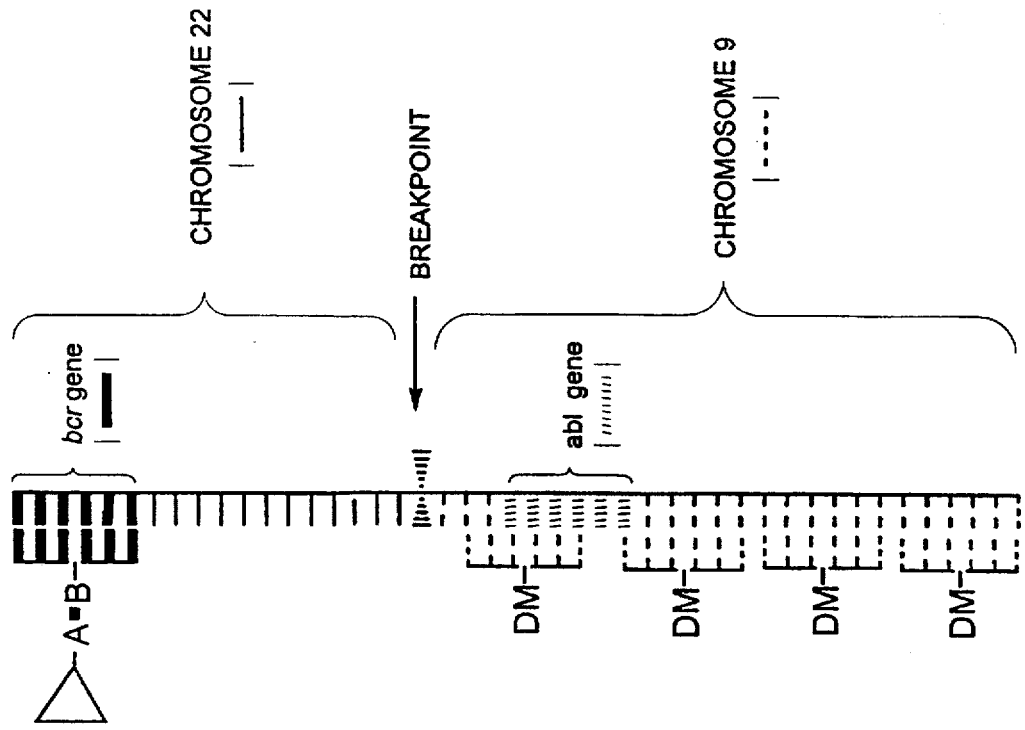
Figure 4A:
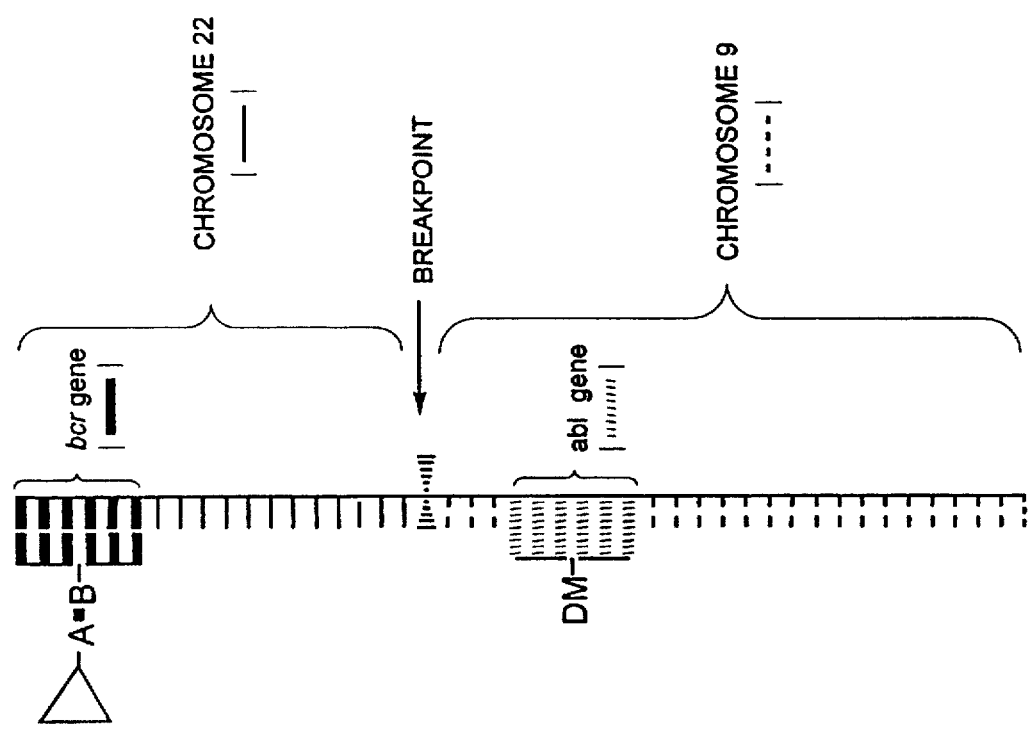

In an alternative embodiment of this example, the second hybridization probe may be formed of a composite of nucleic acid sequences specific for chromosome 9. As illustrated in FIG. 4A, when the second hybridization probe is specific for the abl gene, the second hybridization probe only hybridizes to a small portion of the translocated portion of chromosome 9. However, as illustrated in FIG. 4B, by using a composite second hybridization probe for chromosome 9, multiple second hybridization probes can hybridize to the immobilized DNA containing the Philadelphia chromosome. By multiplying the number of second hybridization probes hybridized to the immobilized Philadelphia chromosome, the amount of detectable marker immobilized is also increased. This serves to greatly increase the sensitivity of the assay.

While the present invention is disclosed by reference to the preferred embodiments and example detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for detecting nucleic acid aberrations in a sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the method comprising:

a) contacting a first hybridization probe which includes a nucleic acid sequence complementary to the first region and a first complexing agent capable of attaching to a second complexing agent with a sample of chromosomal DNA under conditions favorable for hybridization such that the first hybridization probe hybridizes to chromosomal DNA including a nucleic acid sequence from the first region;

b) contacting a second hybridization probe which includes a detectable marker and a nucleic acid sequence complementary to the second region with the sample of chromosomal DNA under conditions favorable for hybridization such that the second hybridization probe hybridizes to chromosomal DNA in the sample which include a nucleic acid sequence from the second region selectively over chromosomal DNA which include a nucleic acid sequence from the first region;

c) contacting a second complexing agent attached to a solid support with the first complexing agent attached to the first hybridization probe such that the first and second complexing agents become attached, thereby immobilizing the first hybridization probe on the solid support; and d) after performing steps a-c in any order, detecting any detectable marker attached to the second hybridization probe which is immobilized on the solid support by the hybridization of the second hybridization probe to chromosomal DNA containing nucleic acid sequences from the first region which are hybridized to the first hybridization probe which is immobilized on the solid support, the first and second hybridization probes being selected such that the presence of a detectable marker immobilized on the solid support indicates the presence of a nucleic acid sequence aberration without indicating the sequence of the region connecting the first and second regions.

2. The method according to claim 1 wherein the first hybridization probe is a whole-chromosome composite probe.

3. The method according to claim 2 wherein the second hybridization probe is a whole-chromosome composite probe.

4. The method according to claim 1 wherein the first complexing agent is selected from the group consisting of antigens, antibodies, biotin, biotin derivatives and analogues, avidin and avidin derivatives and analogues.

5. The method according to claim 1 wherein the detectable marker is selected from the group consisting of a radioisotope, a fluorescent molecule, a chemiluminescent molecule, an antibody and an enzymatically modifiable substrate, the modified enzymatic substrate being analytically detectable.

6. The method according to claim 5 wherein the detectable marker is $^{14}C$, the step of detecting any detectable marker including performing accelerator mass spectroscopy to detect $^{14}C$.

7. The method according to claim 1 wherein the first hybridization probe is contacted with the sample of nucleic acids at the same time that the second hybridization probe is contacted with the sample of nucleic acids.

8. The method according to claim 1 wherein the first hybridization probe is contacted with the sample of nucleic acids prior to contacting the second hybridization probe with the sample of nucleic acids.

9. The method according to claim 1 wherein the second hybridization probe is contacted with the sample of nucleic acids prior to contacting the first hybridization probe with the sample of nucleic acids.

10. The method according to claim 1 wherein the attachment between the first and second complexing agents is detachable, the step of detecting the detectable marker including:
   a) detaching the first and second complexing agents, thereby releasing the detectable marker from the solid support; and
   b) detecting any detectable marker released from the solid support.

11. The method according to claim 1 wherein the first complexing agent is attached to the first hybridization probe by a bond which is detachable, the step of detecting the detectable marker including:
   a) detaching the first complexing agent and the first hybridization probe, to release the detectable marker from the solid support; and
   b) detecting any detectable marker released from the solid support.

12. The method according to claim 1 wherein the step of detecting the detectable marker includes:
   a) dehybridizing the first hybridization probe from the immobilized nucleic acid to release the detectable marker from the solid support; and
   b) detecting any detectable marker released from the solid support.

13. The method according to claim 1 wherein the step of detecting the detectable marker includes:
   a) dehybridizing the second hybridization probe from the immobilized nucleic acid to release the detectable marker from the solid support; and
   b) detecting any detectable marker released from the solid support.

14. The method according to claim 1 wherein the detectable marker is attached to the second hybridization probe by a bond which is detachable, the step of detecting the detectable marker including:
   a) detaching the detectable marker and the second hybridization probe to release the detectable marker from the solid support; and
   b) detecting any detectable marker released from the solid support.

15. A method for detecting nucleic acid aberrations in a sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the method comprising:
   a) contacting a sample of chromosomal DNA under conditions favorable for hybridization with a first hybridization probe immobilized on a solid support, the first hybridization probe including a nucleic acid sequence complementary to the first region such that the first hybridization probe hybridizes to and immobilizes chromosomal DNA having a nucleic acid sequence from the first region;
   b) contacting a second hybridization probe which includes a detectable marker and a nucleic acid sequence complementary to the second region with the sample of chromosomal DNA under conditions favorable for hybridization such that the second hybridization probe hybridizes to chromosomal DNA in the sample having a nucleic acid sequence from the second region selectively over chromosomal DNA which include a nucleic acid sequence from the first region;
   c) detecting any detectable marker from the second hybridization probe immobilized on the solid support, the first and second hybridization probes being selected such that the presence of a detectable marker immobilized on the solid support indicates the presence of a nucleic acid sequence aberration without indicating the sequence of the region connecting the first and second regions.

16. The method according to claim 15 wherein the first hybridization probe is detachable from the solid support, the step of detecting the detectable marker including:
   a) detaching the first hybridization probe from the solid support to release the detectable marker from the solid support; and
   b) detecting any detectable marker released from the solid support.

17. The method according to claim 16 wherein the first hybridization probe includes a first complexing agent which attaches the first hybridization probe to the solid support, the first complexing agent being attached to the first hybridization probe by a bond which is detachable, the step of detecting the detectable marker including:
   a) detaching the first complexing agent from the first hybridization probe to release the detectable marker from the solid support; and
   b) detecting any detectable marker released from the solid support.

18. The method according to claim 15 wherein the step of detecting the detectable marker includes:
   a) dehybridizing the first hybridization probe from the immobilized nucleic acid to release the detectable marker from the solid support; and
   b) detecting any detectable marker released from the solid support.

19. The method according to claim 15 wherein the step of detecting the detectable marker includes:
   a) dehybridizing the second hybridization probe from the immobilized nucleic acid to release the detectable marker from the solid support; and
   b) detecting any detectable marker released from the solid support.

20. The method according to claim 15 wherein the detectable marker is attached to the second hybridization probe by a bond which is detachable, the step of detecting the detectable marker including:
   a) detaching the detectable marker and the second hybridization probe to release the detectable marker from the solid support; and

19 b) detecting any detectable marker released from the solid support.

21. The method according to claim 1 wherein the nucleic acid sequence aberration is associated with the occurance of a disease, the method further comprising the step of:
    diagnosing the disease by detecting the presence of the detectable marker indicating the presence of the nucleic acid sequence aberration associated with the occurance of the disease.

22. The method according to claim 21 wherein the disease is cancer identifiable by a nucleic acid sequence involving the first and second regions.

23. The method according to claim 22 wherein the cancer is selected from the group consisting of leukemia, lymphoma, melanoma, prostate cancer and cervical cancer.

24. The method according to claim 22 wherein the first or second nucleic acid sequence type is an oncogene nucleic acid sequence.

25. The method according to claim 21 wherein the first hybridization probe is contacted with the sample of nucleic acids at the same time that the second hybridization probe is contacted with the sample of nucleic acids.

26. The method according to claim 21 wherein the first hybridization probe is contacted with the sample of nucleic acids prior to contacting the second hybridization probe with the sample of nucleic acids.

27. The method according to claim 21 wherein the second hybridization probe is contacted with the sample of nucleic acids prior to contacting the first hybridization probe with the sample of nucleic acids.

28. The method according to claim 15 where the nucleic acid sequence aberration is associated with the occurance of a disease, the method further comprising the step of:
    diagnosing the disease by detecting the presence of the detectable marker indicating the presence of the nucleic acid sequence aberration associated with the occurance of the disease.

29. The method according to claim 28 wherein the disease is cancer identifiable by a nucleic acid sequence involving the first and second regions.

30. The method according to claim 29 wherein the cancer is selected from the group consisting of leukemia, lymphoma, melanoma, prostate cancer and cervical cancer.

31. The method according to claim 29 wherein the first or second nucleic acid region is an oncogene nucleic acid sequence.

32. A kit for detecting nucleic acid aberrations in a sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the kit comprising:
    a) a first hybridization probe including a nucleic acid sequence complementary to a nucleic acid sequence from the first region and a first complexing agent capable of attaching to a second complexing agent such that the first hybridization probe hybridizes to chromosomal DNA which include a nucleic acid sequence from the first region;
    b) a second hybridization probe including a detectable marker and a nucleic acid sequence complementary to a nucleic acid sequence from the second region such that the second hybridization probe hybridizes to chromosomal DNA in the sample which include a nucleic acid sequence from the second region selectively over nucleic acid sequences from the first region, wherein at least one of the first and second hybridization probes is a composite probe of at least a region of a chromosome and wherein simultaneous hybridization of the first and second probes to chromosomal DNA indicates the presence of a nucleic acid sequence aberration without indicating the sequence of the region connecting the first and second regions; and
    c) a second complexing agent attached to a solid support.

33. The kit according to claim 32 wherein the kit further includes instructions for detecting nucleic acid sequences which include a nucleic acid sequence aberration.

34. The kit according to claim 32 wherein the first hybridization probe is a whole-chromosome composite probe.

35. The kit according to claim 34 wherein the second hybridization probe is a whole-chromosome composite probe.

36. The kit according to claim 32 wherein the first complexing agent is selected from the group consisting of antigens, antibodies, biotin, biotin derivatives and analogues, avidin and avidin derivatives and analogues.

37. The kit according to claim 32 wherein the solid support is formed of a material selected from the group consisting of glass, silica gel, cellulose, nitrocellulose papers, nylon, polystyrene, polymethacrylate, latex, rubber, and fluorocarbon resins.

38. The kit according to claim 32 wherein the detectable marker is selected from the group consisting of a radioisotope, a fluorescent molecule, a chemiluminescent molecule, an antibody and an enzymatically modifiable substrate, the modified enzymatic substrate being analytically detectable.

39. The kit according to claim 32 wherein the attachment between the first and second complexing agents is detachable.

40. The kit according to claim 32 wherein the first complexing agent is attached to the first hybridization probe by a bond which is detachable.

41. The kit according to claim 32 wherein the detectable marker is attached to the second hybridization probe by a bond which is detachable.

42. A kit for diagnosing a disease from a sample of chromosomal DNA, the presence of which is identifiable by the presence of a nucleic acid sequence aberration in the sample of chromosomal DNA characterized by a rearrangement which forms a nucleic acid sequence which includes a first sequence unique to a first region of a chromosome, a second sequence unique to a second, different region of the same chromosome or a different chromosome and a region connecting the first and second regions which includes a site of the rearrangement, the kit comprising:
    a) a first sequence specific hybridization probe including a first complexing agent capable of attaching to a second complexing agent and a first nucleic acid sequence which selectively hybridizes to chromosomal DNA in the sample which include a nucleic acid sequence from the first region;
    b) a second hybridization probe including a detectable marker and a nucleic acid sequence complementary to the nucleic acid sequence from the second region such that the second hybridization probe hybridizes to chromosomal DNA in the sample which include a nucleic acid sequence from the second region selectively over chromosomal DNA which include a nucleic acid sequence from the first region, wherein at least one of the first and second hybridization probes is a composite probe of at least a region of a chromosome and wherein simultaneous hybridization of the first and second probes to chromosomal DNA indicates the presence of a disease without indicating the sequence of the region connecting the first and second regions; and c) a second complexing agent attached to a solid support.

43. The kit according to claim 42 wherein the second hybridization probe selectively hybridizes to a specific sequence of the second type.

44. The kit according to claim 42 wherein the disease is cancer.

45. The kit according to claim 42 wherein the cancer is selected from the group consisting of leukemia, lymphoma, melanoma, prostate cancer and cervical cancer.

46. The kit according to claim 42 wherein the first or second specific sequence encodes for an oncogene.

47. A kit for detecting nucleic acid sequences in a sample of chromosomal DNA which include a chromosome translocation, the chromosome translocation being characterized by a nucleic acid sequence which includes a first sequence unique to a first chromosome, a second sequence unique to a second, different chromosome and a region connecting the first and second regions which includes a site of the translocation, the kit comprising:

a) a first hybridization probe including a first complexing agent capable of attaching to a second complexing agent and a nucleic acid sequence complementary to a nucleic acid sequence unique to the first chromosome such that the first hybridization probe hybridizes to chromosomal DNA which include a nucleic acid sequence unique to the first chromosome;

b) a second hybridization probe including a detectable marker and a nucleic acid sequence at least partially complementary to a nucleic acid sequence unique to the second chromosome such that the second hybridization probe hybridizes to [nucleic acids] chromosomal DNA in the sample which include a nucleic acid sequence unique to the second chromosome selectively over chromosomal DNA which include a nucleic acid sequence unique to the first chromosome, wherein at least one of the first and second hybridization probes is a composite probe of at least a region of a chromosome and wherein simultaneous hybridization of the first and second probes to chromosomal DNA indicates the presence of a chromosome translocation without indicating the sequence of the region connecting the first and second regions; and c) a second complexing agent attached to a solid support.

48. A method for detecting nucleic acid aberrations in a sample of chromosomal DNA characterized by a nucleic acid sequence which includes a first sequence unique to a first chromosome, a second sequence unique to a second, different chromosome and a region connecting the first and second regions, the method comprising:

a) contacting a first hybridization probe which includes a nucleic acid sequence complementary to a nucleic acid sequence unique to the first chromosome and a first complexing agent capable of attaching to a second complexing agent with a sample of chromosomal DNA under conditions favorable for hybridization such that the first hybridization probe hybridizes to chromosomal DNA including a nucleic acid sequence unique to the first chromosome;

b) contacting a second hybridization probe which includes a detectable marker and a nucleic acid sequence complementary to a nucleic acid sequence unique to the second chromosome with the sample of chromosomal DNA under conditions favorable for hybridization such that the second hybridization probe hybridizes to chromosomal DNA in the sample which include a nucleic acid sequence unique to the second chromosome selectively over chromosomal DNA which include a nucleic acid sequence unique to the first chromosome;

c) contacting a second complexing agent attached to a solid support with the first complexing agent attached to the first hybridization probe such that the first and second complexing agents become attached, thereby immobilizing the first hybridization probe on the solid support; and d) after performing steps a-c in any order, detecting any detectable marker attached to the second hybridization probe which is immobilized on the solid support by the hybridization of the second hybridization probe to chromosomal DNA containing nucleic acid sequences of the first region which are hybridized to the first hybridization probe which is immobilized on the solid support, the first and second hybridization probes being selected such that the presence of a detectable marker immobilized on the solid support indicates the presence of a nucleic acid sequence aberration without indicating the sequence of the region connecting the first and second regions.

49. A method for detecting nucleic acid aberrations in a sample of chromosomal DNA characterized by a nucleic acid sequence which includes a first sequence unique to a first chromosome, a second sequence unique to a second, different chromosome and a region connecting the first and second regions, the method comprising:

a) contacting a sample of chromosomal DNA under conditions favorable for hybridization with a first hybridization probe immobilized on a solid support, the first hybridization probe including a nucleic acid sequence complementary to a nucleic acid sequence unique to the first chromosome such that the first hybridization probe hybridizes to and immobilizes chromosomal DNA having a nucleic acid sequence unique to the first chromosome;

b) contacting a second hybridization probe which includes a detectable marker and a nucleic acid sequence at least partially complementary to a nucleic acid sequence unique to the second chromosome with the sample of chromosomal DNA under conditions favorable for hybridization such that the second hybridization probe hybridizes to chromosomal DNA in the sample having a nucleic acid sequence unique to the second chromosome selectively over chromosomal DNA having a nucleic acid sequence unique to the first chromosome;

c) detecting any detectable marker from the second hybridization probe immobilized on the solid support, the first and second hybridization probes being selected such that the presence of a detectable marker immobilized on the solid support indicates the presence of a nucleic acid sequence aberration without indicating the sequence of the region connecting the first and second regions.

50. The method according to claim 1 wherein at least one of the first and second hybridization probes is a composite probe of at least a region of a chromosome.

51. The method according to claim 50 wherein the first and second hybridization probes are composite probes of at least a region of a chromosome.

* * * * *